United States Patent [19]

Webster

[11] Patent Number: 4,820,755

[45] Date of Patent: Apr. 11, 1989

[54] RADIATION STERILIZABLE COMPOSITION AND ARTICLES MADE THEREFROM

[75] Inventor: Joseph R. Webster, Closter, N.J.

[73] Assignee: American Cyanamid Company, Stamford, Conn.

[21] Appl. No.: 86,746

[22] Filed: Aug. 18, 1987

[51] Int. Cl.[4] .......................... C08K 5/34; C08K 5/09; C08K 5/10; C08K 5/36

[52] U.S. Cl. ...................................... 524/88; 524/101; 524/287; 524/291; 524/303; 524/304; 524/305; 524/343; 522/79; 604/199

[58] Field of Search .................... 522/79; 524/88, 101, 524/291, 303, 304, 305, 287, 343; 604/199

[56] References Cited

U.S. PATENT DOCUMENTS

| | | | |
|---|---|---|---|
| 3,537,967 | 11/1970 | Kelley | 524/303 |
| 3,708,457 | 1/1973 | Needham et al. | 524/88 |
| 4,282,076 | 8/1981 | Boynton | 522/79 |
| 4,467,065 | 8/1984 | Williams et al. | 604/199 |

FOREIGN PATENT DOCUMENTS

| | | | |
|---|---|---|---|
| 147039 | 8/1984 | Japan | 524/88 |

*Primary Examiner*—John Kight
*Assistant Examiner*—Kriellion Morgan
*Attorney, Agent, or Firm*—Roger S. Benjamin

[57] ABSTRACT

This invention provides polymers containing radiochromic hindered phenolic stabilizers which are characterized by including a blue compound which interacts with the hindered phenolic during irradiation to provide a color change indicative of sterility.

23 Claims, No Drawings

RADIATION STERILIZABLE COMPOSITION AND ARTICLES MADE THEREFROM

FIELD OF THE INVENTION

This invention relates to radiation sterilizable compositions and sterilized medical instruments made therefrom. More particularly, it pertains to polymers containing a radiochromic stabilizer system which consists of a blue colorant and a hindered phenolic compound which produces a color change during irradiation indicative of sterility.

BACKGROUND OF THE INVENTION

Polymers, such as polyolefins, and especially polyproylene, are widely used to prepare a number of molded articles, such as medical instruments, and especially syringes. These medical instruments are designed to be packaged in sterile containers, opened, used once, and discarded. Conventional ways of sterilizing them, employing steam or ethylene oxide, for example, have the drawbacks of distorting the article because of heat, or requiring the use of somewhat toxic gases. Widely used now are high energy irradiation processes, in which the packaged instrument is exposed to gamma irradiation, e.g., from a cobalt-60 source, or to electron beams, e.g., from a suitable generator. Unfortunately, sterilizing doses, especially of gamma rays, embrittles most polymers, and this is manifested by a decrease in elongation, noted for example, by breaking when a syringe is buckled and/or bent.

The problem of brittle failure after radiation has been overcome in a number of ways. In one, the polymer is mixed with a so-called "mobilizing additive" which is typically a mineral oil. See, for example, Williams et al., U.S. Pat. No. 4,274,932. This has the drawback that the articles are not stable during long term storage, e.g., in warehouses, as determined, for example, in accelerated oven aging tests. Another approach is to use stabilizing additives, such as hindered phenols, as is described for example in Rekers, U.S. Pat. No. 4,460,445. These turn yellow on exposure to sterilization dosages, and this is undesirable. Thiodipropionic acid esters were used by themselves, for improving the color of radiation stabilized articles made from polyolefins, as described in Kelley et al., U.S. Pat. No. 3,537,967, but when used in combination with a hindered phenol, namely 2,6-di-t-butyl-4-methylphenol, the sterilized article became badly discolored, i.e., yellowish to bright yellow. European Patent Application No. 0-087-294, publsihed Aug. 31, 1983, discloses that the use of heterocyclic hindered amines in polyolefins helps to prevent yellow discoloration, but the addition of mineral oil is beneficial in combination to reduce discoloration and embrittlement during irradiation. In this case, long term thermal oxidative stability is compromised by addition of mineral oil.

Of special interest is the disclosure of European Patent Application No. 0-069-342, published Jan. 12, 1983. This discloses that medical equipment can be made from polymers which contain indicators for sterilization treatments. For example, if polyethylene or polypropylene is mixed with hindered phenols, according to this patent, and then molded and subjected to ionizing radiation from a cobalt-60 source, the color changes from colorless to bright yellow and thus the sterile equipment can be differentiated from equipment that has not been sterilized. The drawback in such a process is primarily that the medical profession has a strong aversion to the use of yellow or bright yellow instruments in a hospital environment. Moreover, yellow coloration in polymers is evidence, almost universally accepted, of polymer degradation, not just as a result of irradiation, but also stemming from adverse exposure to heat, light, chemicals, and the like.

It is contemplated by the present invention to provide an improved composition by using a polypropylene of a special type in conjunction with a phenolic stabilizer which is radiochromic, i.e., one which has a tendency to severely discolor whether under high energy radiation or under the normal course of its free radical reaction in the polymer, and incorporating in said composition a low level of a compound, e.g., a dye or a pigment, which will complement the discoloration species of the phenolic and produce an alternate color in the resin, and to articles molded therefrom, which is entirely aesthetically acceptable, while still maintaining the desirable physical properties and clarity of the polymer during and after irradiation with high doses of energy, and during prolonged storage, e.g., of six (6) months or more, for example, in a warehouse.

SUMMARY OF THE INVENTION

According to the present invention, there are provided improved, radiation sterilizable compositions of the type comprising (a) a semi-crystalline polymer having a narrow molecular weight distribution; and, an effective, radiation stabilizing amount of (b) a radiochromic hindered phenolic stabilizer, said improvement comprising using as said polymer a polypropylene having an initial melt flow of below about 5 and including in said composition, (c) a blue compound in an amount sufficient to form a green color by interaction with said radiochromic hindered phenolic stabilizer after said composition has been subjected to a sterilizing dose of gamma irradiation.

A further principal aspect of this invention comprises a medical instrument, e.g., asyringe, sterilized by gamma irradiation, and made from the improved composition as defined above.

Among the preferred features of the invention are compositions in which the radiochromic hindered phenolic stabilizer comprises from about 0.01 to 1 part by weight per 100 parts by weight of said polymer, more preferably from about 0.1 to about 0.3 parts by weight per 100 parts by weight of said polymer. The blue compound preferably comprises from about 1 to about 13 parts by weight per $10^6$ parts by weight of said polymer, most preferably, from about 4 to about 8 parts by weight per $10^6$ parts by weight of said polymer. Also contemplated as embodiments are compositions as above defined which optionally include (d) an effective amount of a co-stabilizer for (b) of an organic thioester or thioether; and (e) an effective amount of an organic ultraviolet radiation stabilizer for said composition, or a mixture of (d) and (e). Preferably, the polypropylene will be a controlled rheology polypropylene, especially preferably one which had, initially, a melt flow of below about 5 grams per 10 minutes at 230° C. according to ASTM D-1238, Condition L. Most preferably the melt flow will be in the range of 0.01 to 1. Special mention is made of polypropylenes having a final melt flow of between about 5 and about 50.

The controlled rheology polypropylene when molded should use mold temperatures in the range from 230° C. to 240° C. and mold quench temperatures below 15° C., preferably between 24° C. and 38° C.

In preferred features, the radiochromic phenolic stabilizer compound comprises a compound of the formula

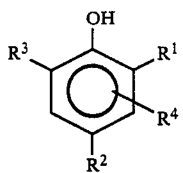

wherein $R^1$, $R^2$, $R^3$ and $R^4$ are substituents on penols which are known in the art to provide oxidative and chemical stabilization of polyolefin, and said compound turns yellow when exposed to a sterilizing dose of gamma radiation. Among these special mention is made of (i) a 3,5-di-t-butyl-4-hydroxyphenyl dihydrocinnamic acid ester of a long chain alcohol, (ii) a 3,5-di-t-butyl-4-hydroxyphenyl dihydrocinnamic acid ester of pentaerythritol, (iii) 1,3,5-tris(4-t-butyl-3-hydroxy-2,6-dimethylbenzyl)-s-triazine-2,4,6(1H, 3H, 5H)-trione, or a mixture of any of (i), (ii) and (iii) or a combination thereof with 2,2'-methylene-bis-6-tert-butyl-p-cresol. Most preferred is (iii) 1,3,5-tris(4-t-butyl-3-hydroxy-2,6-dimethylbenzyl)-s-triazine-2,4,6-(1H, 3H, 5H)-trione.

The preferred blue compounds for this invention are selected from a diazo condensation violet; a quinacridone magenta; carbozole dioxazine violet; a vat blue or a vat violet; a phthalocyanine blue; an iron blue or a disperse blue dye; a chromium oxide blue; a basic blue of the aryl methane derivative type; an inorganic complex oxide; a solvent blue which is oil soluble; a titanate; or a mixture of any of the foregoing. Of these, copper phthalocyanine blue is especially preferred.

Of these embodiments which optionally contain costabilizer (d), these are preferably $C_{12}$ to $C_{18}$ diesters of thiodipropionic acid, such as distearyl thiodipropionate, dilauryl thiodipropionate, dimyristyl thiodipropionate, or a mixture of any of the foregoing with dilauryl thiodipropionate being most preferred. In the embodiments which optionally contain an ultraviolet radiation stabilizer, these are preferably a hindered benzoate compound, a hindered amine compound, or a mixture thereof, and especially the compounds known as CYASORB ® UV 2908 (3,5-di-tert-butyl-4-hydroxybenzoic acid hexadecyl ester) and/or CYASORB ® UV 3346 (poly(6-morpholino-5-triazine-2,4-diyl)2,2,6,6-tetramethyl-4-piperidyl)imino) hexamethylene ((2,2,6,6-tetramethyl-4-piperidiyl)imino)).

At this time, the combination of properties is most advantageously provided by a composition as above defined which comprises (a) semi-crystalline polypropylene having a narrow molecular weight distribution, a Q in the range of about 3 to about 6 and a melt flow in the range of about 5 to about 50; (b) from about 0.05 to about 0.3 parts by weight per 100 parts by weight of (a) of 1,3,5-tris(4-t-butyl-3-hydroxy-2,6-di-methylbenzyl)s-triazine-2,4,6-(1H, 3H, 5)trione; (c) from about 4 to about 8 parts by weight per $10^6$ parts by weight of (a) of copper phthalocyanine blue; (d) from 0 to about 2.0 parts by weight per 100 parts by weight of (a) dilauryl thiodipropionate or distearyl thiodipropionate; and (e) from 0 to about 0.5 parts by weight per 100 parts by weight of (a) of 3,5-di-tert-butyl-4-hydroxybenzoic acid hexadecyl ester.

DETAILED DESCRIPTION OF THE INVENTION

The semi-crystalline polymers having a narrow molecular weight distribution used in the improved compositions of this invention are commercially available and they also can be made in ways known to those skilled in this art.

The polymers have a crystalline content of 20 to 50%, preferably from 30 to 45%. The polymer may be comprised of one, two or more monomers. As representative examples of suitable polymers, there may be mentioned polymers of propylene (homopolymers and copolymers), ethylene (LLDPE, LDPE, HDPE), oxymethylene, butylene, etc. The preferred polymer is polypropylene. The polypropylene can be prepared, for example, by using a conventional Ziegler-Natta catalyst, or one of the more recently developed "high yield" catalysts.

As used herein, the molecular weight distribution, Q, of the polymer is defined by the ratio of the weight average molecular weight to the number average molecular weight. In accordance with the present invention, in narrow molecular weight polymers, such ratio should not be greater than 11.0, preferably no greater than 9.0 and most preferably no greater than 4.0. The minimum ratio, by definition, is 1.0. As a practical matter, the ratio is at least about 2.0, and, in most cases, the ratio is on the order of from 2.0 to 4.0.

The desired ratios are obtained by using controlled rheology techniques, which are well known. If, for example, a polymer having a broad molecular weight distribution is melt blended with a small amount of an organic peroxide and extruded, the molecular weight distribution will be narrowed. Conventional GPC analysis of molecular weight can be carried out to determine if the distribution is within the "narrow range".

The radiochromic hindered phenolic stabilizers used in the improved composition of the present invention are commercially available or can be made in ways known by those skilled in the art.

The phenolic antioxidant stabilizer is incorporated into the polymer in a stabilizing amount, said stabilizer generally being present in an amount of from about 0.01 to 1 part by weight and preferably from about 0.1 to 0.3 parts by weight. Representative examples of suitable phenol antioxidant stabilizers include, but are not limited to alkylated phenols, such as 2,6-di-t-butyl-4-methylphenol; 2,6-di(alphamethylbenzyl) 4-methylphenol; 4-hydroxymethyl-2,6-di-t-butylphenol; butylated hydroxyanisole; 2-t-butyl-1,4-benzenediol; octadecyl 3,5-di-t-butyl-4-hydroxybenzyl phosphonate; bisphenols, such as 2,2'-methylenebis(4-methyl-6-t-butylphenol); 2,2'-methylenebis[4-ethyl-6-t-butylphenol]; 4,4'-butylidenebis(6-t-butyl-m-cresol); 4,4'-methylenebis(2,6-di-t-butylphenol); 2,2'-methylenebis (4-methyl-6-nonylphenol); 2,2'-methylenebis[6-(1-methylcyclocyclohexyl)-p-cresol]; 4,4'-thiobis(6-t-butyl-o-cresol); thiobisdiethylenebis(3,5-di-t-butyl-4-hydroxy)hydrocinnamate; N,N'-hexamethylenebis(3,5-di-t-butyl-4-hydroxyhydrocinnamide); butyric acid, 3,3-bis(3-t-butyl-4-hydroxyphenyl) ethylene ester; 2,2'ethylidenebis(4,6-di-t-butylphenol), and polyphenols such as 1,3,5-tris(4-t-butyl-3-hydroxyl-2,6-dimethylbenzyl)-1,3,5-triazine-2,4,6-(1H, 3H, 5H)-trione; tetrakis[-methylene (3,5di-t-butyl-4-hydroxyhydrocinnamate]methane; 1,3,5-trimethyl-2,4,6-tris(3,5,-di-t-butyl-4-hydroxybenzyl)benzene); tris(3,5,-di-t-butyl-4- hydroxybenzyl)isocyanurate; 3,4-di-t-butyl-4-hydroxyhydrocinnamic acid triester with 1,3,5-tris(2-hydroxyethyl)-s-triazine-2-4,6-(1H, 3H, 5H)-trione; 1,1,3-tris (2-methyl-4-hydroxy-5-t-butylphenyl)butane). The preferred phenol antioxidant stabilizers are (i) a ester of a long chain alcohol, (ii) a 3,5-di-t-butyl-4-hydroxyphenyl dihydrocinnamic acid ester of pentaerythitol, (iii) 1,3,4-tris(4-t-butyl-3-hydroxy-2,6-dimethylbenzyl)-s-triazine-2,4-(1H, 3H, 5H)-trione, or a mixture of any of (i), (ii) and (iii), and most preferred is 1,3,5-tris(4-t-butyl-3-hydroxy-2,6-dimethylbenzyl)-s-triazine-2,4-(1H, 3H, 5H)-trione.

The normal effect of phenolic antioxidants in polypropylene exposed to high energy radiation is to cause a yellow discoloration of the resin.

Discoloration of the resin by the phenolic stabilizer is used to the advantage of the present invention through the use of a low level of a blue compound which will complement the discoloration species of the phenolic stabilizer and cause an alternate color which is aesthetic while maintaining the polymer's physical properties after irradiation. Because of the yellow discoloration by the phenolic stabilizer, a blue dye or pigment is used to create an aesthetic green color upon irradiation.

Representative examples of suitable blue compounds include, but are not limited to, diazo condensation violets, quinacridone magentas, carbazole dioxazine violet, vat blues and vat violets, phthalocyanine blue, iron blue or disperse blue dyes, chromium oxide blues, basic blues of aryl methane derivatives, inorganic complex oxides, solvent blues which are oil soluble and titanates, which can be used alone or in mixtures. Of these examples, most preferred is copper phthalocyanine blue. Levels of the blue compound should be in an amount from about 1 to about 13 parts per million parts by weight, and more preferred from about 4 to about 8 parts per million by weight. Incorporation into the polymer causes a cool blue color which turns to light green and, if conditions are met, to a darker green, upon irradiation. This green color is aesthetically pleasing and accepted in a hospital environment. Color change from blue to green also serves as an indicator that the articles have been radiation sterilized.

Stabilization of the polymer for irradiation can be provided by the radiochromic phenolic antioxidant alone, as described above, or in combination with an organic thioester. Representative examples include, but are not limited to distearyl thiodipropionate, dilauryl thiodipropionate, dimyristyl thiodipropionate and mixtures thereof. The preferred organic thioester and/or thioether for use in this invention is dilauryl thiodipropionate. The organic thioester stabilizer is optionally added to the polymer in an amount from about 0 to about 2.0 parts by weight.

Another optional additive to the radiation sterilizable polymer of the present invention is an ultraviolet radiation stabilizer. Representative examples of ultraviolet radiation stabilizers include, but are not limited to hindered benzoate compounds, polymeric hindered amine compounds or mixtures thereof. These compounds are commercially available or can be made by methods known to one skilled in the art. Of those, preferred compounds commercially available are Cyasorb ® UV-2908 (3-5-di-tert-butyl-4-hydroxybenzoic acid hexadecyl ester) and Cyasorb ® UV-3346 (poly(6-morpholino 5-triazine-2,4-diyl)2,2,6,6-tetramethyl-4-piperidyl)imino) hexamethylene((2,2,6,6-tetramethyl-4-piperidyl)imino)). These compounds should be used in amounts of from 0 to about 0.5 parts per hundred parts by weight of the polypropylene.

Preferred colors can be achieved through the use of a two-component stabilizers system. Of the two component systems those preferred are Cyanox ® 1790 (1,3,5-tris(4-t-butyl-3-hydroxy-2,6-dimethylbenzyl)-s-triazine-2,4,6-(1H, 3H, 5H)-trione and Cyasorb ® UV-2908 (3,5-di-tert-butyl-4-hydroxybenzoic acid hexadecyl ester), Cyanox ® 1790 (1,3,5-tris(4-t-butyl-3-hydroxy-2,6-dimethylbenzyl)-s-triazine-2,4,6-(1H, 3H, 5H)-trione and distearyl thiodipropionate, Cyanox ® 1790 (1,3,5-tris(4-t-butyl-3-hydroxy-2,6-dimethylbenzyl)-s-triazine-2,4,6-(1H, 3H, 5H)-trione and dilauryl thiodipropionate and most preferred is the combination of Cyanox ® 1790 (1,3,5-tris(4-t-butyl-3-hydroxy-2,6-dimethylbenzyl)-s-triazine-2,4,6-(1H, 3H, 5H)-trione and dilauryl thiodipropionate. Deeper shades of olive green have been achieved with Cyanox ® 2246 (2,2-methylene-bis(4-methyl-6-t-butyl)phenol alone and in combination with a thioester of Cyasorb ® UV-2908 (3,5-di-tert 4-hydroxybenzoic acid hexadecyl ester).

The improved composition, containing some or all of the above described additives, can be employed to produce an article which is to be sterilized by procedures known in the art. As representative examples of such articles, not intending to limit the invention in any way, are syringes, tube assemblies sutures, tissue culture flasks, needles, non-woven multifilament fibers for gowns, package film, etc.

Sterilization of articles produced from the composition of the present invention can be achieved by subjecting the polymer, with the above identified additives incorporated therein, to a sterilizing amount of high energy radiation. The high energy radiation can be provided by any one of a number of sources, including cobalt-60, high energy electrons and x-rays. In general, the sterilization dosages are on the order of from 0.5 to 5.0 megarads, with the typical dose being 1.0 to 3.5 megarads, for example, at dose rates of 0.2 to 5 megarads per hour. It is to be understood that higher doses can be employed but are generally not necessary, or even desirable.

It has been found that by incorporating the teachings of the present invention, the sterilized or irradiated polymer not only possess an aesthetic color but also retains the physical properties of the polymer. In this regard, the retention of elongation and color of a treated article produced from the present invention is maintained over storage periods of six months or longer.

The invention will be further described with respect to the following examples; however, the scope of the invention is not to be limited thereby.

DESCRIPTION OF THE PREFERRED EMBODIMENT

The following examples illustrate the present invention but are not intended to limit the claims in any manner whatsoever.

In the following examples, the following Trademarks, Tradenames and abbreviations have the following meanings:

CYANOX ® 2246 Antioxidant—2,2′-methylene-bis(4-methyl-6-t-butyl)phenol

CYANOX ® 1790 Antioxidant—1,3,5-tris(4-t-butyl-3-hydroxy-2,6-dimethylbenzyl)-s-triazine-2,4,6-(1H, 3H, 5H)-trione;

CYASORB ® UV 2908 Light Stabilizer—3,5-di-tert-butyl-4-hydroxybenzoic acid hexadecyl ester;

CYASORB ® UV 3346 Light Stabilizer—poly(6-morpholino-5-triazine-2,4-diyl)2,2,6,6-tetramethyl-4-piperidyl)imino) hexamethylene ((2,2,6,6-tetramthyl-4-piperidyl)-imino))

DLTDP—dilauryl thiodipropionate

DSTDP—distearyl thiodipropionate

EXAMPLE 1

(a) A low melt flow semi-crystalline polypropylene (M.F.=3-4) is treated with an organic peroxide in the melt to cleave the high molecular weight fraction and to reduce the polydisperisty, Q, to a value below 6. The melt flow of the final polymer is 23-24. The actual procedure to prepare a controlled rheology polymer suitable for use in this invention is as follows:

(b) A composition is prepared by dry blending and then melt blending in a ¾ inch Haake extruder at 232° C. at 100 rpm, the following:

| Compound | Parts by Weight |
|---|---|
| Polypropylene powder (as in step (a)) | 100 |
| CYANOX ® 1790 antioxidant | 0.1 |
| Dilauryl thiodipropionate | 1.0 |
| Copper phthalocyanine blue | 0.0013 |
| Calcium stearate (mold release) | 0.1 |

The extruded composition is chopped into pellets, shaken in a polyethylene bag and injection molded 24-48 hours after extrusion. The conditions for molding were 230°-250° C. with 1000 psi forward pressure and 150 psi back pressure. The mold temperature was 38° C. The specimens comprise 60 mil plaques. They are subjected to elongation testing by pulling a microtensile specimen cut from the plaque parallel to the flow lines. The pulling rate is two inches per minute at a 2 inch gauge length. They are also subjected to irradiation sterilization using a 3 million curie cobalt-60 source at a dose rate of 1.5 Mrads/hour. Elongation is also measured on the irradiated specimens after exposure to 1.5 Mrads and 3.5 Mrads of radiation. The results are as follows:

| | |
|---|---|
| After 1.5 Mrads exposure: | 96% retention of elongation (593% to 570%) Color change from blue to green |
| After 3.5 Mrads exposure: | 88% retention of elongation (593% to 523%) Color change from blue to green |

EXAMPLE 2

Following the general procedure of Example 1, the following components were used:

| Compounds | Parts by Weight |
|---|---|
| Polypropylene powder | 100 |
| CYANOX ® 1790 Antioxidant | 0.1 |
| DSTDP | 1.0 |
| blue pigment | 0.0005 |
| calcium stearate | 0.1 |
| Final melt flow - 19-20. | |
| The results are as follows: | |
| After 2.5 Mrads exposure: | 100% retention of elongation. (531% to 576%) |
| After 3.5 Mrads exposure: | 60% retention of elongation. (531% to 300%) |

Initial Visual Color—Pale Blue

Instrumental Initial Color(b)=−0.8

After 1.5 Mrads Visual Color—Pale Blue Green

Instrumental Color after 1.5 Mrads—b=2.0

After 3.5 Mrads Visual color—Light Green

Instrumental Color after 3.5 Mrads—b=5.3

EXAMPLE 3

Following the general procedure of Example 1, the following components were used:

| Compounds | Parts by Weight |
|---|---|
| Polypropylene powder (0.5 melt flow) | 100 |
| CYANOX ® 1790 Antioxidant | 0.2 |
| DLTDP | 1.0 |
| blue pigment | 0.0005 |
| calcium stearate | 0.1 |
| Final melt flow - 22. | |
| Results: | |
| After 1.5 Mrads at 1.5 Mrads/hour: | 100% retention of elongation. (525% to 525%) |
| After 3.5 Mrads at 3.5 Mrads/hour: | 70% retention of elongation. (525% to 360%) |

Initial Visual Color—Pale Blue green.

Instrumental color—b=0.3

Visual Color after 1.5 Mrads—Pale green

Instrumental color after 1.5 Mrads—b=1.8

Visual Color after 3.5 Mrads—Light green

Instrumental color after 3.5 Mrads—b=6.4

Results from 1 year, dark, room temperatue storage: After 3.5 Mrads at 1.5 Mrads/hours; 100% retention of elongation.

EXAMPLE 4

Following the general procedure of Example 1, the following components were used:

| Compound | Parts by Weight |
|---|---|
| Polypropylene powder | 100 |
| CYANOX ® 2246 Antioxidant | 0.2 |
| blue pigment | 0.0007 |
| calcium stearate | 0.1 |
| Final melt flow - 16. | |
| Results: | |
| After 1.5 Mrads at 1.5 Mrads/hour: | 95% retention of elongation (603% to 575%) |

Initial Visual Color—Blue Green

Instrumental Initial Color—b=7.1

Visual color after 1.5 Mrads—Slight blue green

Instrumental color after 1.5 Mrads—b=11

Visual color after 3.5 Mrads—Olive Green intense

Instrumental color after 3.5 Mrads—b=22

EXAMPLE 5

Following the general procedure of Example 1, the following components were used:

| Compound | Parts by weight |
|---|---|
| Polypropylene powder | 100 |
| CYANOX ® 2246 Antioxidant | 0.2 |
| DLTDP | 1.0 |
| blue pigment | 0.0007 |
| calcium stearate | 0.1 |
| Results: | |
| Final Melt Flow - 10 | |
| After 2.5 Mrads at 1.5 Mrads/hour: | 93% retention of elongation (520% to 483%) |
| After 3.5 Mrads at 1.5 Mrads/hour: | 94% retention of elongation (520% to 491%) |
| After 5.0 Mrads at 1.5 Mrads/hour: | 93% retention of elongation (520% to 485%) |
| Final Melt Flow - 15 | |
| After 2.5 Mrads at 1.5 Mrads/hour: | 95% retention of elongation (523% to 497%) |
| After 3.5 Mrads at 1.5 Mrads/hour: | 89% retention of elongation (523% to 468%) |
| After 5.0 Mrads at 1.5 Mrads/hour: | 82% retention of elongation (523% to 428%) |
| Final Melt Flow - 20 | |
| After 2.5 Mrads at 1.5 Mrads/hour: | 87% retention of elongation (574% to 500%) |
| After 3.5 Mrads at 1.5 Mrads/hour: | 74% retention of elongation (574% to 425%) |
| After 5.0 Mrads at 1.5 Mrads/hour: | 7% retention of elongation (574% to 38%) |

EXAMPLE 6

Following the general procedure of Example 1, the following components were used:

| Compound | Parts by Weight |
|---|---|
| Polypropylene powder | 100 |
| CYANOX ® 1790 Antioxidant | 0.1 |
| DSTDP | 0.5 |
| blue pigment | 0.0005 |
| calcium stearate | 0.1 |
| Final Melt Flow - 17. | |
| Results: | |
| After 1.5 Mrads at 1.5 Mrads/hour: | 98% retention of elongation (543% to 533%) |
| After 3.5 Mrads at 3.5 Mrads/hour: | 55% retention of elongation (543% to 300%) |

Initial Visual Color—Very Pale Blue
Instrumental Initial—b=0.5
After 1.5 Mrads Visual—Pale Blue Green
Instrumental after 1.5 Mrads—b=2
After 3.5 Mrads Visual—Pale Green.
Instrumental after 3.5 Mrads—b=5

The following formulations will produce compositions within the scope of this invention:

EXAMPLE 7

| Compound | Parts by Weight |
|---|---|
| Polypropylene powder | 100 |
| CYANOX ® 1790 Antioxidant | 0.2 |
| blue pigment | 0.0007 |
| calcium stearate | 0.05 |
| Initial Melt Flow - 0.5 | |
| Final Melt Flor - 15 | |
| Results: | |
| After 3.5 Mrads at 1.5 Mrads/hour: | 100% retention of elongation |
| After 5.0 Mrads at 1.5 Mrads/hour: | 92% retention of elongation |
| Results from 1 year, dark, room temperature storage: | |
| 3.5 Mrad sample: | 91% retention of elongation |
| 5.0 Mrad sample: | 10% retention of elongation |

EXAMPLE 8

| Compound | Parts by Weight |
|---|---|
| Polypropylene powder | 100 |
| CYANOX ® 1790 Antioxidant | 0.2 |
| blue Pigment | 0.0007 |
| calcium stearate | 0.05 |
| Initial Melt Flow - 3.0 | |
| Final Melt Flow - 13 | |
| Results: | |
| After 3.5 Mrads at 1.5 Mrads/hour: | 80% retention of elongation |

EXAMPLE 9

| Compound | Parts by Weight |
|---|---|
| Polypropylene powder | 100 |
| CYANOX ® 1790 Antioxidant | 0.2 |
| DLTDP | 1.0 |
| blue pigment | 0.0007 |
| calcium stearate | 0.05 |
| Initial Melt Flow | 0.5 |
| Final Melt Flow | 12 |
| Results: | |
| After 3.5Mrads at 1.5Mrads/hour: | 100% retention of elongation |
| After 5.0Mrads at 1.5Mrads/hour: | 99% retention of elongation |
| Results after 1 year, dark, room temperature storage: | |
| 3.5Mrad sample: | 99% retention of elongation |
| 5.0Mrad sample: | 100% retention of elongation |

EXAMPLE 10

| Compound | Parts by Weight |
|---|---|
| Polypropylene powder | 100 |
| CYANOX ® 1790 Antioxidant | 0.2 |
| CYANOX ® 2246 Antioxidant | 0.05 |
| DLTDP | 1.0 |
| blue pigment | 0.0007 |
| calcium stearate | 0.05 |
| Initial Melt Flow | 3.0 |
| Final Melt Flow | 13 |
| Results: | |
| After 2.5Mrads at 1.5Mrads/hour: | 100% retention of elongation |
| After 3.5Mrads at 1.5Mrads/hour: | 100% retention of elongation |
| Results after 1 year, dark, room temperature storage: | |
| 2.5 Mrad sample: | 70% retention of elongation |
| 3.5 Mrad sample: | 50% retention of elongation |

-continued

| Compound | Parts by Weight |
|---|---|
| 5.0 Mrad sample: | 10% retention of elongation |

EXAMPLE 11

| Compound | Parts by Weight |
|---|---|
| Polypropylene powder | 100 |
| CYANOX ® 1790 Antioxidant | 0.1 |
| CYASORB ® UV 3346 Light Stabilizer | 0.1 |
| DLTDP | 0.3 |
| blue pigment | 0.0007 |
| calcium stearate | 0.05 |
| Initial Melt Flow - 3.0 | |
| Final Melt Flow - 13 | |
| Results: | |
| After 2.5 Mrads at 1.5 Mrads/hour: | 60% retention of elongation |
| After 3.5 Mrads at 1.5 Mrads/hour: | 50% retention of elongation |
| After 5.0 Mrads at 1.5 Mrads/hour: | 10% retention of elongation |

EXAMPLE 12

| Compound | Parts by Weight |
|---|---|
| Polypropylene powder | 100 |
| CYANOX ® 1790 Antioxidant | 0.2 |
| CYASORB ® UV 3346 Light Stabilizer | 0.1 |
| DLTDP | 0.3 |
| blue pigment | 0.0007 |
| calcium stearate | 0.05 |
| Initial Melt Flow - 0.5 | |
| Final Melt Flow - 13 | |
| Results: | |
| After 3.5 Mrads at 1.5 Mrads/hour: | 92% retention of elongation |
| After 5.0 Mrads at 1.5 Mrads/hour: | 48% retention of elongation |
| Results after 1 year, dark, room temperature storage: | |
| 3.5 Mrad sample: | 52% retention of elongation |
| 5.0 Mrad sample: | 60% retention of elongation |

EXAMPLE 13

| Compound | Parts by Weight |
|---|---|
| Polypropylene powder | 100 |
| CYANOX ® 1790 Antioxidant | 0.2 |
| CYASORB ® UV 2908 Light Stabilizer | 0.2 |
| DLTDP | 1.0 |
| blue pigment | 0.0007 |
| calcium stearate | 0.05 |
| Initial Melt Flow - 3.0 | |
| Final Melt Flow - 13 | |
| Results: | |
| After 2.5 Mrads at 1.5 Mrads/hour: | 100% retention of elongation |
| After 3.5 Mrads at 1.5 Mrads/hour: | 91% retention of elongation |
| After 5.0 Mrads at 1.5 Mrads/hour: | 74% retention of elongation |
| Results after 1 year, dark, room temperature storage: | |
| 2.5 Mrad sample: | 75% retention of elongation |
| 3.5 Mrad sample: | 60% retention of elongation |
| 5.0 Mrad sample: | 25% retention of elongation |

EXAMPLE 14

| Compound | Parts by Weight |
|---|---|
| Polypropylene powder | 100 |
| CYANOX ® 1790 Antioxidant | 0.2 |
| CYASORB ® UV 2908 Light Stabilizer | 0.3 |
| DLTDP | 1.0 |
| blue pigment | 0.0007 |
| calcium stearate | 0.05 |
| Initial Melt Flow - 3.0 | |
| Final Melt Flow - 13 | |
| Results: | |
| After 3.5 Mrads at 1.5 Mrads/hour: | 94% retention of elongation |
| After 5.0 Mrads at 1.5 Mrads/hour: | 88% retention of elongation |
| Results after 1 year, dark, room temperature storage: | |
| 3.5 Mrad sample: | 94% retention of elongation |
| 5.0 Mrad sample: | 43% retention of elongation |

EXAMPLE 15

| Compound | Parts by Weight |
|---|---|
| Polypropylene powder | 100 |
| CYANOX ® 1790 Antioxidant | 0.1 |
| CYASORB ® UV 2908 Light Stabilizer | 0.3 |
| blue pigment | 0.0007 |
| calcium stearate | 0.05 |
| Initial Melt Flow - 3.0 | |
| Final Melt Flow - 13 | |
| Results: | |
| After 2.5 Mrads at 1.5 Mrads/hour: | 60% retention of elongation |
| After 3.5 Mrads at 1.5 Mrads/hour: | 50% retention of elongation |

EXAMPLE 16

| Compound | Parts by Weight |
|---|---|
| Polypropylene powder | 100 |
| CYANOX 1790 Antioxidant | 0.2 |
| CYASORB ® UV 2908 Light Stabilizer | 0.3 |
| DLTDP | 1.0 |
| blue pigment | 0.0007 |
| calcium stearate | 0.05 |
| Initial Melt Flow - 3.0 | |
| Final Melt Flow - 20 | |
| Initial Melt Flow - 3.0 | |
| Final Melt Flow - 30 | |
| Results: | |
| After 2.5 Mrads at 1.5 Mrads/hour: | 100% retention of elongation |
| After 3.5 Mrads at 1.5 Mrads/hour: | 96% retention of elongation |
| After 5.0 Mrads at 1.5 Mrads/hour: | 65% retention of elongation |
| Results after 1 year, dark, room temperature storage: | |
| 2.5 Mrad sample: | 100% retention of elongation |
| 3.5 Mrad sample: | 100% retention of elongation |
| Results with the 3.0 to 30 range were somewhat lower. | |

EXAMPLE 17

| Compound | Parts by Weight |
|---|---|
| Polypropylene powder | 100 |
| CYANOX ® 2246 Antioxidant | 0.2 |
| DLTDP | 1.0 |
| blue pigment | 0.0007 |
| calcium stearate | 0.05 |
| Initial Melt Flow - 3.0 | |

-continued

| Compound | Parts by Weight |
|---|---|
| Final Melt Flow - 13 | |
| Initial Melt Flow - 3.0 | |
| Final Melt Flow - 20 | |
| Results (with 3-13 melt flow change): | |
| After 2.5 Mrads at 1.5 Mrads/hour: | 100% retention of elongation |
| After 3.5 Mrads at 1.5 Mrads/hour: | 90% retention of elongation |
| After 5.0 Mrads at 1.5 Mrads/hour: | 82% retention of elongation |
| Results after 1 year, dark, room temperature storage: | |
| 2.5 Mrad sample: | 91% retention of elongation |
| 3.5 Mrad sample: | 41% retention of elongation |
| Results (with 3-20 melt flow change) | |
| After 2.5 Mrads at 1.5 Mrads/hour: | 100% retention of elongation |
| After 3.5 Mrads at 1.5 Mrads/hour: | 75% retention of elongation |
| After 5.0 Mrads at 1.5 Mrads/hour: | 10% retention of elongation |

EXAMPLE 18

| Compound | Parts by Weight |
|---|---|
| Polypropylene powder | 100 |
| CYANOX ® 1790 Antioxidant | 0.2 |
| CYASORB ® UV 2908 Light Stabilizer | 0.3 |
| DSTDP | 1.0 |
| blue pigment | 0.0007 |
| calcium stearate | 0.05 |
| Initial Melt Flow - 3.0 | |
| Final Melt Flow - 13 | |
| Results: | |
| After 2.5 Mrads at 1.5 Mrads/hour: | 100% retention of elongation |
| After 3.5 Mrads at 1.5 Mrads/hour: | 95% retention of elongation |
| After 5.0 Mrads at 1.5 Mrads/hour: | 90% retention of elongation |
| Results after 1 year, dark, room temperature storage: | |
| 2.5 Mrad sample: | 100% retention of elongation |
| 3.5 Mrad sample: | 95% retention of elongation |
| 5.0 Mrad sample: | 42% retention of elongation |

The foregoing patents, publications and test methods are incorporated herein by reference.

Many variations will suggest themselves to those skilled in this art in light of the above description. For example, instead of CYANOX® 1790, there can be used octadecyl 3,5-di-t-butyl-4-hydroxyhydrocinnamate. Instead of copper phthalocyanine blue there can be used carbazole dioxazine violet. All such obvious variations are within the full intended scope of the appended claims.

I claim:

1. An improved radiation sterilizable composition of the type comprising (a) a semi-crystalline polymer having a narrow molecular weight distribution; and an effective, radiation stabilizing amount of (b) a radiochromic hindered phenolic stabilizer, said improvement comprising using as said polymer a controlled-rheology polypropylene having a melt flow of greater than about 5 and including in said composition (c) a blue compound in an amount sufficient to form in the composition a green color by interaction with said radiochromic hindered phenolic stabilizer after said composition has been subjected to a sterilizing dose of gamma irradiation.

2. A composition as defined in claim 1 wherein said radiochromic hindered phenolic stabilizer comprises from about 0.01 to 1 part by weight per 100 parts by weight of said polymer.

3. A composition as defined in claim 2 wherein said radiochromic hindered phenolic stabilizer comprises from about 0.1 to about 0.3 parts by weight per 100 parts by weight of said polymer.

4. A composition as defined in claim 1 wherein said blue compound comprises from about 1 to about 13 parts by weight per $10^6$ parts by weight of said polymer.

5. A composition as defined in claim 4 wherein said blue compound comprises from about 4 to about 8 parts by weight per $10^6$ parts by weight of said polymer.

6. A composition as defined in claim 1 which optionally includes additives selected from:

(d) an effective amount of co-stabilizer for (b) of an organic thioester or thioether;

(e) an effective amount of an organic ultraviolet radiation stabilizer for said composition;

(f) a mixture of (d) and (e).

7. A composition as defined in claim 1 wherein said polypropylene is a controlled rheology polypropylene.

8. A composition as defined in claim 7 wherein said controlled rheology polypropylene had, initially, a melt flow of below about 5.

9. A composition as defined in claim 8 wherein said polypropylene had, initially, a melt flow in the range of 0.01 to 1.

10. A composition as defined in claim 7 wherein said polypropylene has a final melt flow of between about 5 and about 50.

11. A composition as defined in claim 1 wherein said radiochromic hindered phenolic stabilizer comprises a compound of the formula

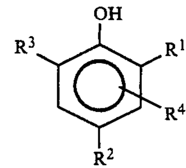

wherein $R^1$, $R^2$, $R^3$ and $R^4$ are substituents on phenols to provide oxidative and chemical stabilization of polyolefins, and said compound turns yellow when exposed to a sterilizing dose of gamma radiation.

12. A composition as defined in claim 11 wherein said radiochromic hindered phenolic stabilizer comprises (i) a 3,5-di-t-butyl-4-hydroxyphenyl dihydrocinnamic acid ester of a long chain alcohol, (ii) a 3,5-di-t-butyl-4-hydroxyphenyl dihydrocinnamic acid ester of pentaerythitol, (iii) 1,3,5-tris(4-t-butyl-3-hydroxy-2,6-dimethylbenzyl)-s-triazine-2,4,6-(1H, 3H, 5H)-trione, or a mixture of any of (i), (ii) and (iii), alone, or in further combination with 2,2'-methylene bis 6-tert-butyl-p-cresol.

13. A composition as defined in claim 12 wherein said radiochromic hindered phenolic stabilizer comprises (iii) 1,3,5-tris(4-t-butyl-3-hydroxy-2,6-di-methylbenzyl)-s-triazine-2,4,6-(1H, 3H, 5H)-trione.

14. A composition as defined in claim 1 wherein said blue compound is selected from a diazo condensation violet; a quinacridone magenta; carbozole dioxazine violet; a vat blue or a vat violet; a phthalocyanine blue; an iron blue or a disperse blue dye; a chromium oxide blue; a basic blue of the aryl methane derivative type; an inorganic complex oxide; a solvent blue which is oil soluble; a titanate; or a mixture of any of the foregoing.

15. A composition as defined in claim 14 wherein said blue compound comprises copper phthalocyanine blue.

16. A composition as defined in claim 6 wherein said organic thioester (d) comprises distearyl thiodipropionate, dilauryl thiodipropionate, dimyristyl thiodipropionate or a mixture of any of the foregoing.

17. A composition as defined in claim 16 wherein said organic thioester comprises dilauryl thiodipropionate.

18. A composition defined in claim 6 wherein said ultraviolet radiation stabilizer comprises a hindered benzoate compound, a polymeric hindered amine compound, or a mixture thereof.

19. A composition as defined in claim 18 wherein said stabilizer comprises 3,5-di-tert-butyl-4-hydroxybenzoic acid hexadecyl ester.

20. A composition as defined in claim 18 wherein said stabilizer comprises poly (6-morpholino-5-triazine-2,4-diyl)2,2,6,6-tetramethyl-4-piperidyl)imino) hexamethylene((2,2,6,6-tetramethyl-4-piperidiyl)imino)).

21. A composition as defined in claim 1 comprising (a) a semi-crystalline polypropylene having a narrow molecular weight distribution having a Q in the range of from about 3 to about 6 and a melt flow range of from about 10 to about 25;

(b) from about 0.05 to 0.3 parts by weight per 100 parts by weight of (a) of 1,3,5-tris(4-t-butyl-3-hydroxy-2,6-dimethylbenzyl)-s-triazine-2,4,6-(1H, 3H, 5H)-trione;

(c) from about 4 to about 8 parts by weight per $10^6$ parts by weight of (a) of copper phthalocyanine blue;

(d) from 0 to about 2.0 parts by weight per 100 parts by weight of (a) of dilauryl thiodipropionate or distearyl thiodipropionate; and (e) from 0 to about 0.5 parts by weight per 100 parts by weight of (a) of 3,5-di-tert-butyl-4-hydroxybenzoic acid hexadecyl ester.

22. A medical instrument sterilized by gamma irradiation made from the improved composition defined by claim 1.

23. A medical instrument as defined in claim 22 wherein said medical instrument is a syringe.

* * * * *